US00PP15953P3

(12) United States Plant Patent
van Haastest

(10) Patent No.: US PP15,953 P3
(45) Date of Patent: Sep. 13, 2005

(54) ***CLEMATIS* PLANT NAMED 'VANSO'**

(50) Latin Name: ***Clematis* hybrid**
Varietal Denomination: Vanso

(75) Inventor: Frans C. M. van Haastest, Holland (NL)

(73) Assignee: Pride of Place Plants, Sidney (CA)

( * ) Notice: Subject to any disclaimer, the term of this patent is extended or adjusted under 35 U.S.C. 154(b) by 122 days.

(21) Appl. No.: 10/029,663

(22) Filed: Dec. 18, 2001

(65) Prior Publication Data

US 2003/0115650 P1 Jun. 19, 2003

(51) Int. Cl.[7] ..... A01H 5/00
(52) U.S. Cl. ..... Plt./228
(58) Field of Search ..... Plt./228

*Primary Examiner*—Kent Bell
(74) *Attorney, Agent, or Firm*—Christie, Parker & Hale, LLP

(57) ABSTRACT

Described as a new variety of *Clematis* which produces fully doubled flowers of attractive coloration.

2 Drawing Sheets

Latin name of genus: The botanical classification of the new *Clematis* plant is *Clematis* hybrid. Variety denomination:

The new plant has the varietal denomination 'Vanso'.

BACKGROUND OF THE INVENTION

The present invention relates to a new *Clematis* plant having the varietal denomination 'Vanso'. 'Vanso' was discovered as a natural branch mutation of the variety 'Mrs. Chalmondeley', not known to be patented.

SUMMARY OF THE INVENTION

The new variety is a *Clematis* plant with a climbing habit distinguished by production of fully double flowers. Asexual reproduction of the new variety as performed by softwood cuttings in Boskoop, The Netherlands has confirmed that the distinguishing characteristics of the new variety are transmitted through succeeding generations and asexually reproduced plants of the new variety reproduce true-to-type.

COMPARISON WITH PARENT

The new variety differs from its parent, 'Mrs. Chalmondeley', in producing flowers which are fully double; whereas flowers of the parent variety are single.

BRIEF DESCRIPTION OF ILLUSTRATIONS

The accompanying illustrations depict plants of the new variety in color as true as possible in color photographic illustrations of this nature.

FIG. 1 shows the plant of the new variety with a cluster of flowers; and

FIG. 2 shows a close up of the flower of the new variety.

DETAILED DESCRIPTION OF THE NEW VARIETY

The following is a description of the new variety taken from 2-year-old plants grown out-of-doors in 5 liter containers in Boskoop, The Netherlands during the month of June. Color designations used herein are from The Royal Horticultural Society Colour Chart ("R.H.S.C.") . The age of the plants used for the description is 2 years and were grown in 5 liter containers.

PLANT

The plant grows in a climbing habit and attains a height of slightly more than 2 M. with an average diameter of about 35 cm. and with vigorous growth.

Foliage:

*Size.*—About 5 cm. to 8 cm. long, up to about 4.8 cm. wide.

*Quantity.*—About 6 leaves (3 pairs of opposite leaves) per about 15 cm. stem.

*Leaf.*—Average length: About 15.3 cm. Average width: About 9.3 cm. Average length of leaflets: About 5 to 8 cm; average about 6.2 cm. Average width of leaflets: About 2.7 to 4.8 cm; average about 3.2 cm. Leaflet apex: Apiculate. Leaflet base: Attenuate to acuminate. Average petiole length: About 7.5 cm. Average petiole width: About 2 mm.

*Color.*—Immature foliage Upper side: Between R.H.S.-CC 141A and 143A. Underside: Between R.H.S.-CC 146A and 146B. Mature foliage Upper side: Near 137A. Under side: Between R.H.S.-CC 137B and 137C.

*Shape.*—Trifoliolate — leaflets are ovate to narrow ovate.

*Texture.*—Upper side: Smooth. Under side: Smooth.

*Venation.*—Anastomosing.

*Edge.*—Smooth with no serration observed.

*Petiole color.*—Top surface: Near 166A. Under side: Between R.H.S.-CC 143A and 141B.

*Stipules.*—No stipules observed.

*Auricles.*—No auricles observed.

*Rachis.*—Smooth.

Stem:

*Average length.*—About 90 cm.

*Average width.*—About 3 mm.

*Texture.*—Smooth, slightly glossy.

*Aspect.*—Ribbed lengthways with an average of 6 ribs.

*Average internode length.*—About 12.6 cm.

*Color of young stem.*—Near R.H.S.-CC 143A to 143C to 144A.

Wood:

*Color.*—Color of new wood green to yellow green — near R.H.S.-CC 143A and 143C to 144A; color of old wood greyed-orange — near R.H.S.-CC 175A to 175B.

*Bark.*—Bark has short pale greyish hairs.

Flower: Not for use as a cut flower.

*Color.*—Clear blue double flowers.

*Shape of buds.*—Ovate.

*Average length of buds.*—About 2.4 cm.

*Average width of buds.*—Abpit 1.4 cm.

*Color of buds.*—Yellow-green, near R.H.S.-CC 145A, with lighter axial stripes near R.H.S.-CC 145D.

*Average number of flowers and buds per plant per season.*—7.

*Flower shape.*—Rotate.

*Average flower diameter.*—About 16.1 cm.

*Average flower depth.*—About 6.7 cm.

*Fragrance.*—Very faint, sweet.

*Tepals.*—Average number: 6 (occasionally 7 or 8). Average length: About 8 cm. Average width: About 4.9 cm. Shape: Obovate. Apex: Mucronulate. Base: Cuneate. Margin: Entire. Color of tepal when young Upper side: Violet-blue; near R.H.S.-CC 92A, tip and central band near the tip near R.H.S.-CC 71B to 71C. Under side: Violet-blue; near R.H.S.-CC 90D, with a broad central band near R.H.S.-CC 145C to 145D (with a slight touch of violet-blue). Color of tepal when mature Upper side: Violet-blue; near R.H.S.-CC 91B with a lighter center near R.H.S.-CC 91D and a small blotch near R.H.S.-CC 71C to 71D at the tip. Under side: Violet-blue; near R.H.S.-CC 91C; margins darker; near R.H.S.-CC 91B and a broad central band near R.H.S.-CC 145C to 145D.

*Tepaloids.*—Average number: About 325. Average length: About 4.2 cm. Average width: Outer (wider): About 1.8 cm. Inner (Narrower): About 4.5 mm. Shape Outer: Obovate. Inner: Linear. Apex Outer: Rounded to praemorse. Inner: Acute. Base: Cuneate. Margin: Entire. Color when young Upper side: Outer tepaloids violet-blue near R.H.S.-CC 92A; tip violet near R.H.S.-CC 86B; inner tepaloids violet near R.H.S.-CC 86B to 86C. Under side: Outer tepaloids violet-blue near R.H.S.-CC 90D, with a broad central band near R.H.S.-CC 145C to 145D; inner tepaloids violet-blue near R.H.S.-CC 91D. Color when mature Upper side: Outer tepaloids violet-blue near R.H.S.-CC 91A with a lighter center near R.H.S.-CC 91B to 91C; inner tepaloids violet-blue near R.H.S.-CC 92A. Under side: Outer tepaloids violet-blue near R.H.S.-CC 91C to 91D, margins darker near R.H.S.-CC 91B and a central blotch near R.H.S.-CC 145D; inner tepaloids violet-blue near 91D.

*Average flower lastingness of individual flower.*—20 days.

*Time to produce a flowering plant.*—12 months.

*Natural flowering season.*—June to September in Boskoop, The Netherlands.

Flowers conpletely double; all reproductive organs transformed into tepaloids. No pollen are formed, no anthers, stigmas, or pistils are present, no fruits or seeds are produced.

Winter hardiness: Winter hardy in USDA Zone 5.

Resistance to disease: No more susceptible to disease than its parent variety or other similar varieties.

Breeding: Asexual reproduction was started from softwood cuttings during the summer months in tunnels. Natural mutation was observed when one branch of the parent variety flowered with double flowers. This mutation branch was then propagated by softwood cuttings.

Stamens, filaments & anthers:

*Arrangement.*—Flowers are completely double, so no stamens, styles, etc. No seed formation observed.

I claim:

1. A new variety of *Clematis* plant as shown and described.

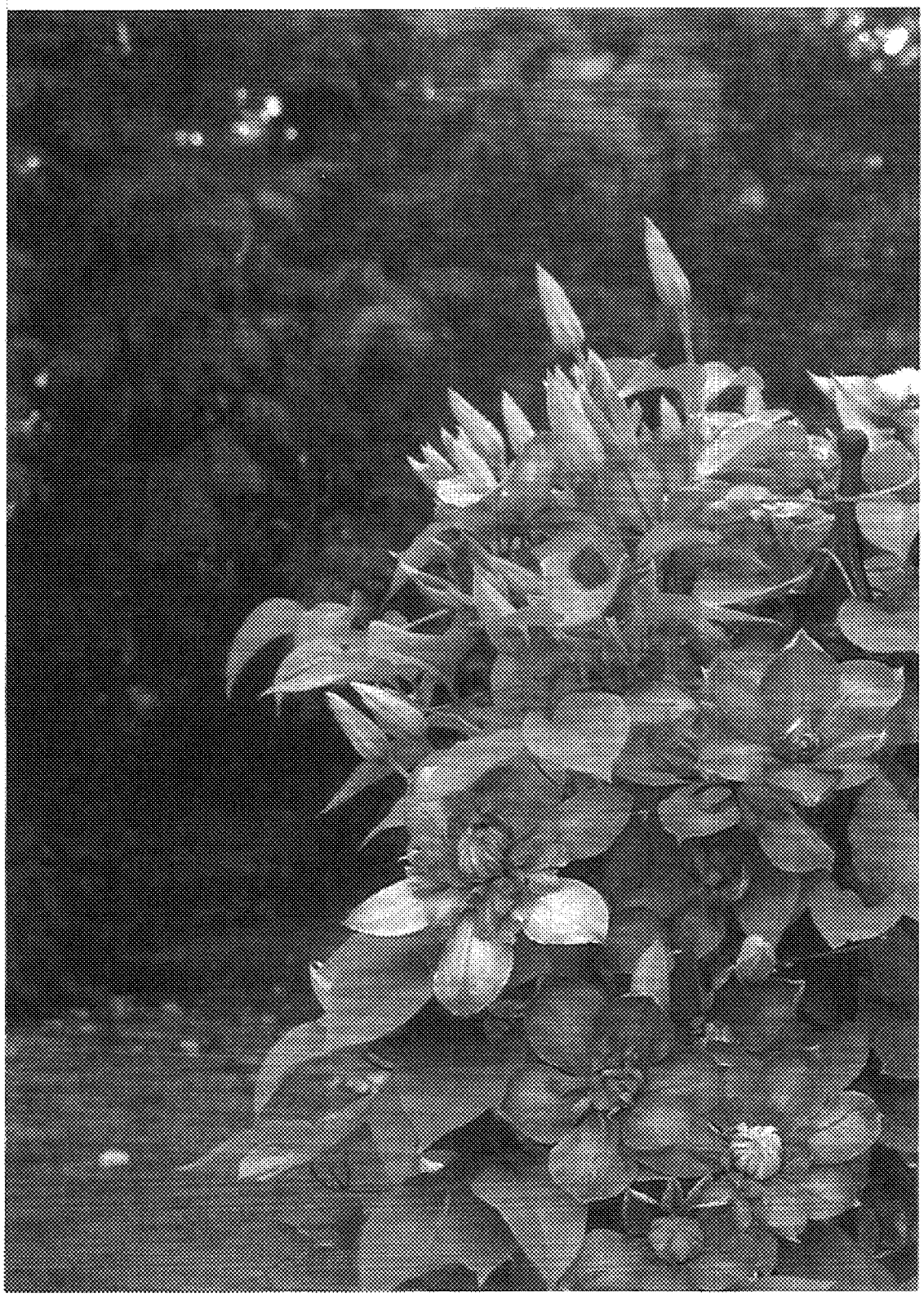

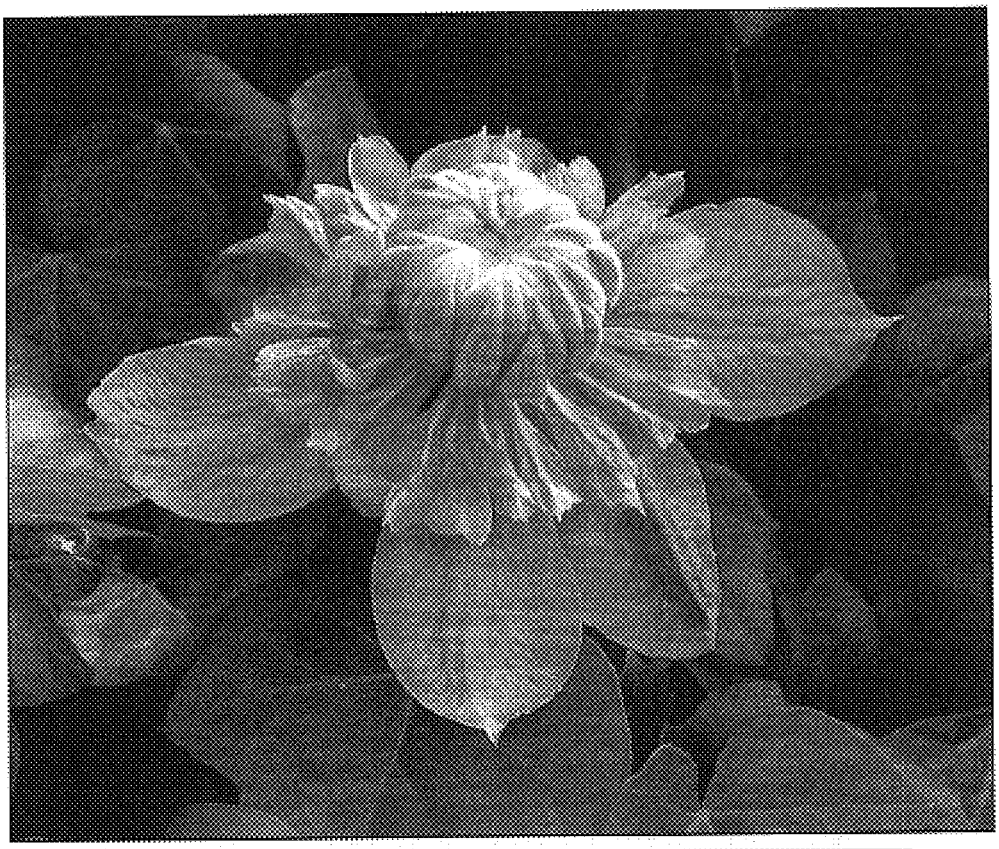
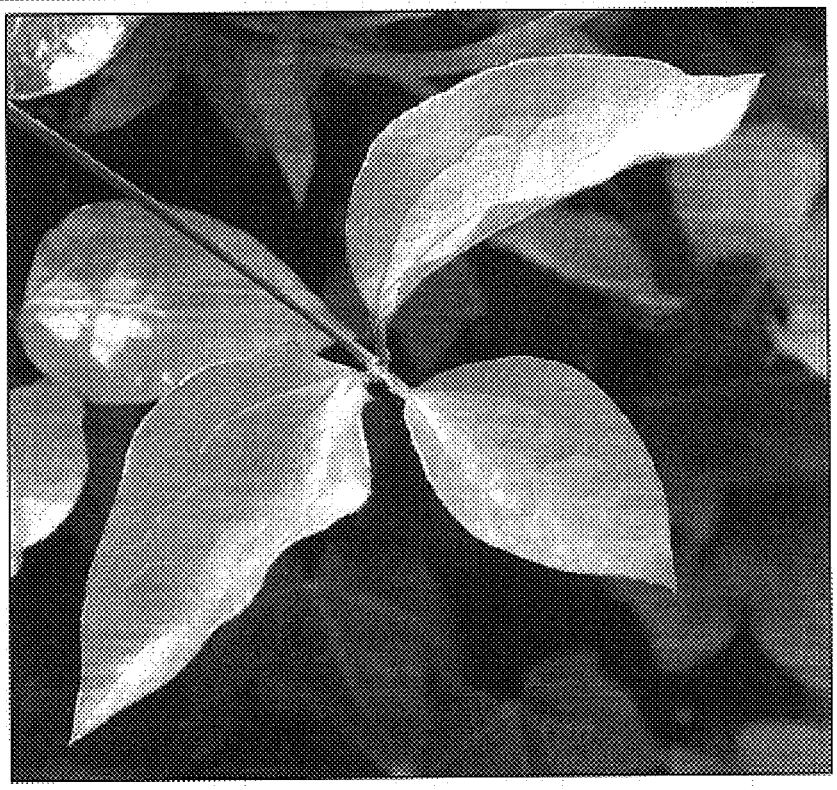

* * * * *